US00PP08489P

United States Patent [19]

Hirabayashi et al.

[11] Patent Number: Plant 8,489

[45] Date of Patent: Dec. 7, 1993

[54] PETUNIA PLANT NAMED 'REVOLUTION PASTELPINK'

[75] Inventors: Hiroshi Hirabayashi, Yachiyo; Yuji Tamura, Yamanashi, both of Japan

[73] Assignees: Keisei Rose Nurseries, Inc., Tokyo; Suntory Limited, Osaka, both of Japan

[21] Appl. No.: 976,372

[22] Filed: Nov. 13, 1992

[51] Int. Cl.[5] ..... A01H 5/00

[52] U.S. Cl. ..... Plt./68.1

[58] Field of Search ..... Plt./68.1

*Primary Examiner*—James R. Feyrer

*Assistant Examiner*—Bruce R. Campell

*Attorney, Agent, or Firm*—Burns, Doane, Swecker & Mathis

[57] ABSTRACT

Disclosed herein is a decumbent type petunia plant having long stems and below-moderate leaves. The plant has abundant branching and a great profusion of blooms, and the whole bush remains in bloom for a considerable period of time. The flowers are single and small and the petals have strong purplish pink color with dull yellow green lines radiating from yellowish white bottom throat portion. The plant is highly resistant to rain, heat, disease and drought.

4 Drawing Sheets

BACKGROUND OF THE VARIETY

The present invention relates to a new and distinct variety of petunia plant obtained from crossing 'Revolution Purplepink' (♀) and one petunia plant (♂) having white color petal which was selected from twice backcrossing of a wild type of petunia native to Brazil as mother plant and 'Recoverer White' as pollen parent.

Petunia is a very popular plant and is used for flower bedding and potting in the summer season. There are only a few varieties of the petunia plant which do not have an upright growth habit and which have a high resistance to rain, heat, drought and cold. Accordingly, this invention was aimed at obtaining a new variety of decumbent habit petunia plant having long stems and large blooms, pink petal color, the bush remaining in bloom for a considerable period of time, and a high resistance to rain, heat, drought and cold.

The new variety of petunia plant according to this invention originated from a crossing of 'Revolution Purplepink', which is a petunia plant bred by the present inventors, as the female parent and one petunia plant (♂) having white color petal which was selected from twice backcrossing of a wild type of petunia native to Brazil as mother plant and 'Recoverer White' as pollen parent, in June, 1988 at the Yachiyo Farm of KEISEI ROSE NURSERIES, Inc., residing at 755 Ōwadasinden, Yachiyo-shi, Chiba-ken, Japan. From this crossing, 350 seedlings were obtained in 1989, from which 5 desired seedlings were selected, propagated by cutting, and then grown as a trial by flower bedding and potting in planters. Only one of the 5 resulting plants was selected, as the most desirable one. The botanical characteristics of the finally-selected plant were then examined, using a comparative variety, female parent 'Revolution Purplepink', for comparison, from the spring of 1990. As a result, it was concluded that this petunia plant is clearly distinguishable from the comparative variety in flower color, while maintaining beneficial characteristics thereof, and it is further distinguishable from any other variety, whose existence is known to us, and this new variety of petunia plant was named 'Revolution Pastelpink'.

In the following description, the color-coding is in accordance with The Horticultural Color Chart of The Royal Horticulatural Society, London, England (RHS Color Chart), and the Japan Color Standard for Horticultural Plant (JHS Color Chart).

The female parent, 'Revolution Purplepink' (see, U.S. Plant Pat. No. 6,915), which originated from a crossing of a wild type of petunia (♀) native to Brazil and 'Recover White' (♂), is presently maintained at the aforementioned Yachiyo Farm of the KEISEI ROSE NURSERIES, Inc., and Plant Biotechnology Laboratory, Institute for Fundamental Research of SUNTORY Ltd., and is world wide marketed. The main botanical characteristics of this female parent are as follows.

Plant:

*Growth habit.*—Decumbent. The stems hang down when potted in a hanging pot.

*Plant height.*—15–20 cm.

*Spreading area of plant.*—The stem extends to a length of 50–80 cm from the base, and thus the spreading area of the plant is 100–150 cm in diameter.

*Growth.*—Very vigorous with abundant branching, a great profusion of blooms; the whole bush remaining in bloom for a considerable period of time.

*Blooming period.*—Late March to late September, in the southern Kantō area, Japan. The plant shape does not change throughout this period.

Stem:

*Thickness.*—Main stem 4.0–6.0 mm; lateral stem 2.0–3.0 mm.

*Color.*—Strong to moderate yellow green (RHS 144B - 143C, JHS 3512-3710).

*Pubescence.*—Normal.

*Branching.*—Over-abundant.

*Length of internode.*—1.0–1.5 cm before blooming; 3.0–4.0 cm during blooming.

Leaf:

*Phyllotaxis.*—Verticillate before blooming; opposite during blooming.

*Shape.*—Lanceolate.

*Size (average).*—7.5–8.0 cm × 2.5–3.0 cm, large.

*Thickness.*—0.5–0.7 mm.

*Color.*—Moderate yellow green (RHS 146B - 137D, JHS 3508 - 3712).

*Pubescence.*—Normal.

Flower: Opening obliquely upward.

*Type.*—Single.

*Shape.*—Funnel-shape, with five-fissured limb.

*Diameter.*—8.0–9.0 cm, large.

*Petal color.*—In the unopened stage (bud), deep to moderate purple (RHS 86A - 83A, JHS 8307 - 8306); when open, vivid reddish purple (RHS 74A, JHS 9207); at full bloom, vivid reddish purple (RHS 71D - 74 B, JHS 9206 - 9207), with strong reddish purple (RHS 72B, JHS 9208) lines radiating from a small brilliant purple (RHS 82C, JHS 8611) area closely proximate to a pale to light yellow green (RHS 4D-145C, JHS 3310 - 3103) center portion. The small area completely surrounds the center portion. The reverse side of the petal is a light purple color (RHS 75B, JHS 8903). The petal has a somewhat metallic luster.

*Reproductive organs.*—1 normal pistil having a grayish yellow green (RHS 138A, JHS 3715) stigma, and 5 normal stamens each having a moderate blue (RHS 98B - 98C, JHS 8305) anther and a purple yellow green (RHS 145D, JHS 3502) filament.

*Peduncle.*—2.0 mm in thickness, and 2.0–2.5 cm in length.

Physiological and ecological characteristics: High resistance to rain, heat and drought. Also high resistance to disease, particularly gray mold (Botrytis). Moderate resistance to pest.

The male parent of this new variety 'Revolutiton Pastelpink' is one petunia plant having white color petal which was selected from twice backcrossing of a wild type of petunia native to Brazil as mother plant and 'Recoverer White' as pollen plant. 'Recoverer White' is one of the Recoverer Series bred by the SAKATA SEED Corp., Japan. The Recover Series includes 'Recoverer Scarletred', 'Recoverer Blue', and 'Recoverer Pink', and these plants are commonly characterized by a high resistance to rain. The main botanical characteristics of 'Recoverer White', are as follows.

Plant:

*Growth habit.*—Upright.

*Plant height.*—30–40 cm.

*Spreading area of plant.*—25–30 cm in diameter.

*Blooming period.*—April to September in the southern Kantō area, Japan.

Stem:

*Thickness.*—Main stem 5.0–7.0 mm; lateral stem 2.5–4.5 mm.

*Color.*—Strong yellow green (RHS 144B - 144 C, JHS 3512 - 3513).

*Branching.*—Abundant.

*Pubescence.*—Normal.

*Length of internode.*—2.0 ∝ 3.0 cm before blooming; 2.0–4.0 cm during blooming.

Leaf:

*Phyllotaxis.*—Verticillate before blooming; opposite during blooming.

*Shape.*—Oval.

*Size (average).*—4.5–5.0 cm×2.5–3.0 cm.

*Thickness.*—0.4–0.6 mm.

*Petal color.*—Strong yellow green to moderate olive green (RHS 144A - 146A, JHS 3507 - 3508).

*Pubescence.*—Few.

Flower: Opening obliquely upward.

*Type.*—Single.

*Shape.*—Funnel-shape, with five-fissuered limb.

*Diameter.*—8.0–8.5 cm.

*Petal color.*—In the unopened stage (bud), pale yellow green (RHS 4D - 157A, JHS 3304 - 3303); both when open and at full bloom, greenish white (RHS 155D - 155C, JHS 3701).

*Reproductive organs.*—1 normal pistil having a strong yellow green (RHS 144B - 144C, JHS 3512) stigma, and 5 normal stamens each having a pale yellow (RHS 161D, JHS 2503) anther and a greenish white (RHS 157D, JHS 3501) filament.

*Peduncle.*—1.5–2.5 mm in thickness, and 2.5–3.0 cm in length.

Physiological and ecological characteristics: High resistance to rain, heat, and disease, and moderate resistance to pest.

This new and distinct variety of petunia plant, 'Revolution Pastelpink', was asexually reproduced by cutting at the aforementioned Yachiyo Farm of KEISEI ROSE NURSERIES, Inc., and Plant Biotechnology Laboratory, Institute for Fundamental Research of SUNTORY Ltd., and the homogeneity and stability thereof were confirmed.

SUMMARY OF THE VARIETY

The new variety of petunia plant has a decumbent habit and long stems and below-moderate leaves, and thus is very distinguishable from a similar variety, 'Recoverer White', having an upright growth habit. The plant has abundant branching and a great profusion of blooms, and the whole bush remains in bloom for a considerable period of time, longer than the blooming period of 'Recoverer White'. The flowers are single and small, smaller than 'Recoverer White' and 'Revolution Purplepink', and the petal color is strong purplish pink which is clearly distinguished from white color of 'Recoverer White' and the vivid red purple color of 'Revolution Purplepink', with dull yellow green lines radiating from yellowish white bottom throat portion. The plant is highly resistant to rain, heat, and drought.

DESCRIPTION OF THE VARIETY

Figure 1:
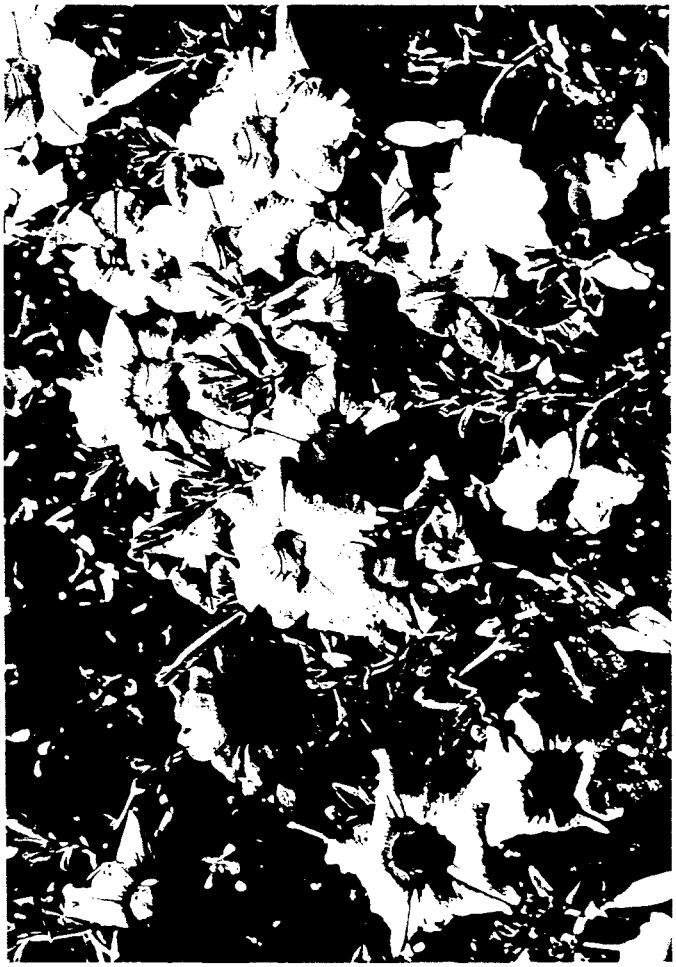
FIG. 1 is a photograph giving a partial view of the new variety of petunia plant planted in a flower bed.
Figure 2:
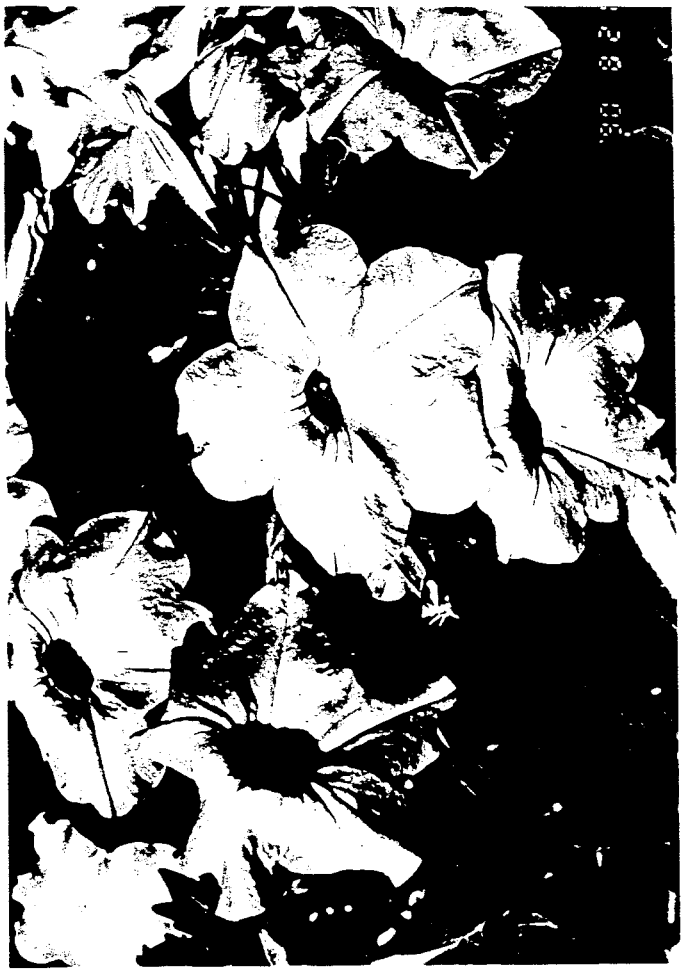
FIG. 2 is a photograph of flowers of the new variety of petunia plant.
Figure 3:
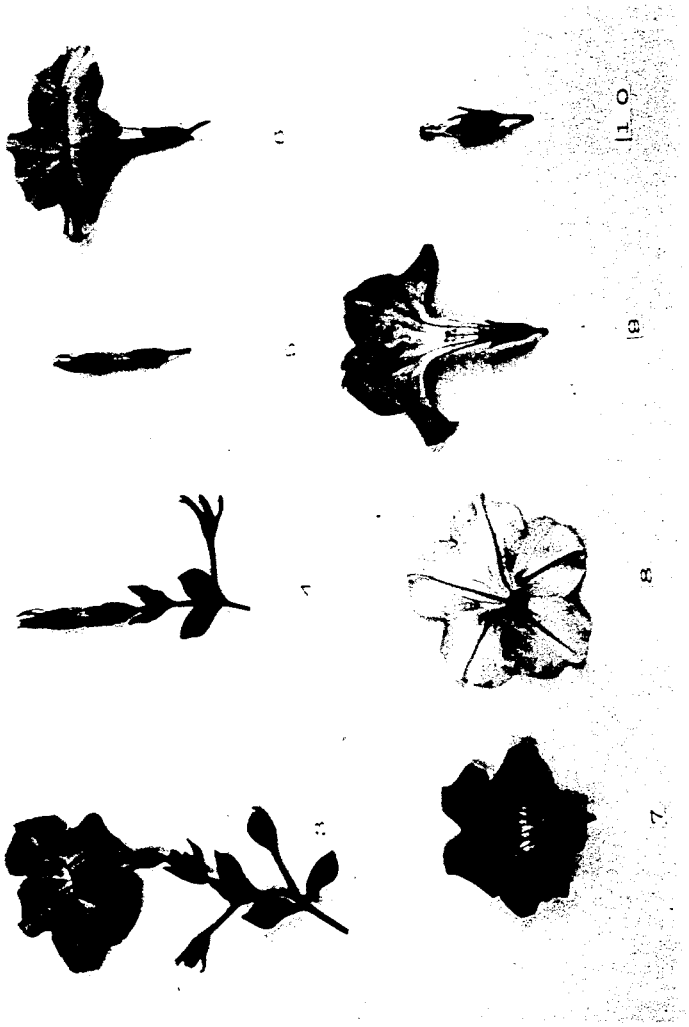
FIG. 3 is a photograph showing, in numerical order, a branch having an open flower (3), a current shoot (4), a bud (5), a side view of the flower (6), a front view of the flower (7), a rear view of the flower (8), an interior view of the flower (9), and pistil and stamens (10), of the new variety of petunia plant.
Figure 4:
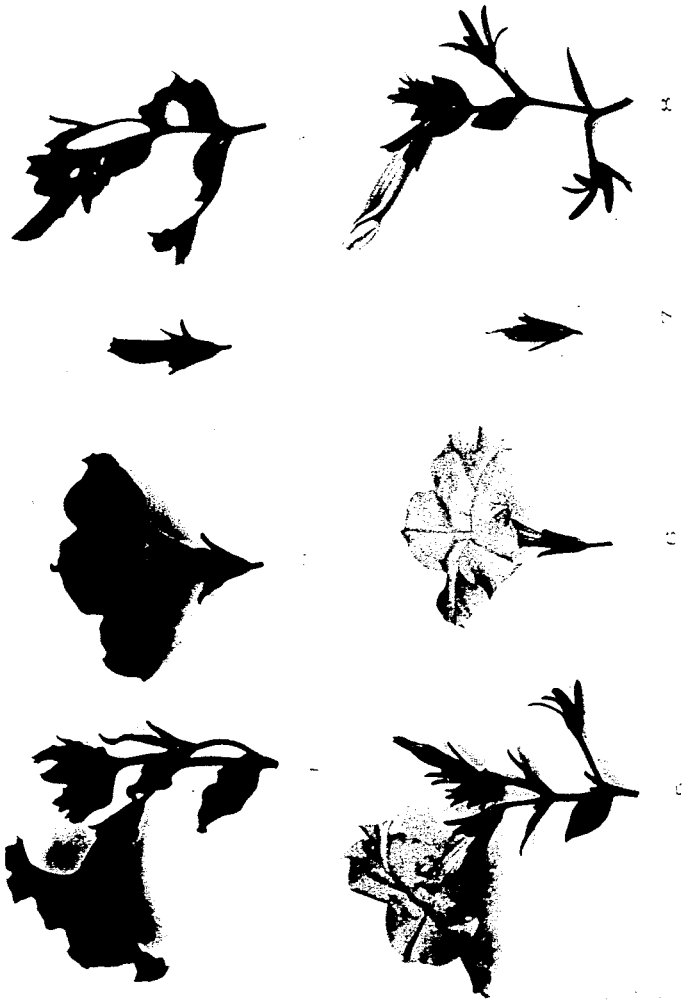
FIG. 4 is a photograph showing, in numerical order, a branch having an open flower (1), a flower (2), a bud (3), and a current shoot (4) of the comparative, 'Revolution Purplepink', in comparison with corresponding items (5–8) of the new variety of petunia plant.

The botanical characteristics of the new and distinct variety of petunia plant 'Revolution Pastelpink' are as follows.

Plant:

*Growth habit.*—Decumbent. The stems hang down when potted in a hanging pot.

*Plant height.*—15–20 cm.

*Spreading area of plant.*—The stem extends to a length of 35–50 cm from the base, and thus the spreading area of the plant is 70–100 cm in diameter.

*Growth.*—Very vigorous with abundant branching, a great profusion of blooms; the whole bush remaining in bloom for a considerable period of time.

*Blooming period.*—Late March to late September, in the southern Kantō area, Japan. The plant shape does not change throughout this period.

Stem:

*Thickness.*—Main stem 3.5–5.0 cm.

*Anthocyanin pigmentation.*—Little present.

*Pubescence.*—Medium.

*Branching.*—Over-abundant.

*Length of internode.*—3.0–3.5 cm.

Leaf:

*Leaf attaching angle.*'Horizontal slightly upward.

*Shape.*—Lanceolate.

*Size (average).*—2.5–4.5 cm×1.5–2.5 cm, below-moderate.

*Thickness.*—0.7 mm.

*Color.*—Dark yellow green (RHS 146A, JHS 3508).

*Pubescence.*—Medium.

Flower: Opening obliquely upward.

*Type.*—Single.

*Shape.*—Funnel-shape, with five-fissured limb.

*Shape of tip.*—Blunt.

*Lobation.*—Shallow.

*Undulation of margin.*—Weak.

*Diameter.*—3.0–4.5 cm, small.

*Petal color.*—At full blooming time, strong purplish pink (RHS 75A, JHS 8904), with dull yellow green (RHS 147B, JHS 3514) lines radiating from yellowish white (RHS 157C, JHS 3302) bottom throat portion. The outside of the petal is a pale purplish pink (RHS 76D, JHS 8902).

*Reproductive organs.*—1 normal pistil and 5 normal stamens. Pistil is medium shape and stamens are medium shape.

*Peduncle.*—2.0 mm in thickness, and 2.0–2.5 cm in length is medium.

Physiological and ecological characteristics: High resistance to rain, heat, cold and drought. Also high resistance to disease, particularly gray mold (Botrytis). Moderate resistance to pest.

This new variety of petunia plant is most suitable for flower bedding and potting, particularly in hanging pots or planters, and further excellent for ground cover.

The plant of this new variety 'Revolution Pastelpink' is presently planted and maintained at the Yachiyo Farm of the KEISEI ROSE NURSERIES, Inc., residing at 755 Ōwadasinden, Yachiyo-shi, Chiba-ken, Japan, and Plant Biotechnology Laboratory, Institute for Fundamental Research of SUNTORY Ltd., residing at 2913-1 Torihara, Hakushu-cho, Kitakoma-gun, Yamanashi-ken, Japan.

We claim:

1. A new and distinct variety of petunia plant, substantially as herein illustrated and described, characterized particularly as to novelty by (A) being a decumbent habit plant having long stems and below-moderate leaves, (B) an abundant branching and a great profusion of blooms, the whole bush remaining in bloom for a considerable period of time, (C) flowers that are single and small, the petals having strong purplish pink color with duall yellow green lines radiating from a small yellowish white bottom throat portion, and (D) a high resistance to rain, heat, drought, and disease.

* * * * *